United States Patent
Vipparla

(10) Patent No.: US 11,328,575 B2
(45) Date of Patent: May 10, 2022

(54) VAPING ALERT SYSTEM

(71) Applicant: Rachna Vipparla, Milford, CT (US)

(72) Inventor: Rachna Vipparla, Milford, CT (US)

( * ) Notice: Subject to any disclaimer, the term of this patent is extended or adjusted under 35 U.S.C. 154(b) by 0 days.

(21) Appl. No.: 17/065,702

(22) Filed: Oct. 8, 2020

(65) Prior Publication Data
US 2021/0110695 A1    Apr. 15, 2021

Related U.S. Application Data

(60) Provisional application No. 62/915,392, filed on Oct. 15, 2019.

(51) Int. Cl.
| | |
|---|---|
| *G08B 21/12* | (2006.01) |
| *G08B 21/18* | (2006.01) |
| *G01N 9/36* | (2006.01) |
| *G01N 33/00* | (2006.01) |

(52) U.S. Cl.
CPC .............. *G08B 21/182* (2013.01); *G01N 9/36* (2013.01); *G01N 33/0063* (2013.01)

(58) Field of Classification Search
CPC ........ G08B 21/182; G08B 21/12; G01N 9/36; G01N 33/0063
See application file for complete search history.

(56) References Cited

U.S. PATENT DOCUMENTS

| 10,024,814 B2 | 7/2018 | Belbruno | |
| 2007/0008099 A1* | 1/2007 | Kimmel | ........... G08B 13/19656 |
| | | | 340/506 |
| 2015/0132857 A1* | 5/2015 | Belbruno | ........... G01N 33/0073 |
| | | | 436/96 |
| 2015/0235539 A1* | 8/2015 | Orvis | ................. G01N 33/0065 |
| | | | 340/632 |
| 2020/0029133 A1* | 1/2020 | Gehlsen | ............. H04N 21/8549 |

OTHER PUBLICATIONS

Davis, Trip, e-mail re "student's vape detector", FreshAir Sensor LLC, May 29, 2019.
Liu, et al., Detection of Secondhand Cigarette Smoke via Nicotine Using Conductive Polymer Films, Nicotine & Tobacco Research, vol. 15, No. 9 (Sep. 2013) 1511-1518.

* cited by examiner

*Primary Examiner* — Hongmin Fan
(74) *Attorney, Agent, or Firm* — McCarter & English, LLP

(57) ABSTRACT

A vaping alert system having a sensor assembly for generating an alert, a digital device having a display for providing a notification to a custodian thereof when an alert is generated, and a computer network for communicating the alert from the sensor assembly to the digital device. The sensor assembly includes a baseboard; a sensor film that has a property of interest that changes a measurable amount upon exposure to a level of nicotine in an atmosphere of a confined space, as arises from the use of an electronic cigarette therein; a transducer associated with the sensor film for detecting a change in the property of interest and generating an electrical signal indicative of a change in the property of interest; and a microcontroller programmed for receiving the electrical signal indicative of a change in the property of interest and for generating an alert when the property of interest exceeds a preselected threshold level. The sensor assembly additionally has an air circulator to assist moving air from the surrounding region over the sensor film, and a power supply for energizing the microcontroller and the air circulator.

11 Claims, 2 Drawing Sheets

VAPING ALERT SYSTEM

CROSS-REFERENCE TO RELATED APPLICATION

This application claims the benefit of U.S. Provisional Application No. 62/915,392, filed Oct. 15, 2019.

BACKGROUND OF THE INVENTION

Field of the Invention

This invention relates to systems for alerting supervisory personnel to unpermitted utilization of electronic cigarettes, also known as "vaping."

Description of the Related Art

Traditional tobacco products, such as pipes, cigars and cigarettes, involve the combustion of tobacco followed by the inhalation of smoke from the combustion.

In recent years, an alternative has arisen in the form of electronic cigarettes. Electronic cigarettes function by vaporizing a mixture of widely varying composition, following which the user inhales the vapor. The ingredients typically include nicotine and a carrier compound such as propylene glycol, as well as other ingredients that may impart a flavor to the vapor.

The use of electronic cigarettes, commonly referred to as "vaping," has become popular among some youths. This has caused great concern, since there may be substantial health risks associated with vaping. In at least one instance, high school students were found to use electronic cigarettes in school bathrooms, causing the school to lock a number of the bathrooms in order to help control the situation.

It has been reported that nicotine entrained in the air can alter a property of polyaniline film upon contact with the film. As a result, it has been proposed to utilize this characteristic to detect second-hand tobacco smoke.

SUMMARY OF THE INVENTION

I have invented a system for alerting supervisory personnel of the use of nicotine-generating material, particularly electronic cigarette use. The system senses nicotine in the air of a room and thereupon sends an alert message to a supervisory authority. For example, if the sensor is placed in a school bathroom, the message would be sent to the school administration, which could then take appropriate measures.

In one aspect, the present invention is directed to a vaping alert system comprising a sensor assembly including a baseboard and a sensor film secured to the baseboard. The sensor film has a property of interest that changes a measurable amount upon exposure to a level of nicotine found in the atmosphere of a confined space, as arises from the use of an electronic cigarette therein. The sensor assembly also includes a transducer associated with the sensor film for detecting a change in the property of interest and generating an electrical signal indicative of a change in the property of interest, a microcontroller programmed for receiving the electrical signal indicative of a change in the property of interest and for generating an alert when the property of interest exceeds a preselected threshold level, an air circulator to assist moving air from the surrounding region over the sensor film, and a power supply for energizing the microcontroller and the air circulator. The vaping alert system additionally features a digital device having a display for providing a notification to a custodian thereof when an alert is generated, and a computer network connected to the microcontroller and the digital device for communicating the alert from the microcontroller to the digital device.

These and other aspects of the present invention are described in the drawings annexed hereto, and in the description of the preferred embodiments and claims set forth below.

DETAILED DESCRIPTION OF THE PREFERRED EMBODIMENTS

Figure 1:
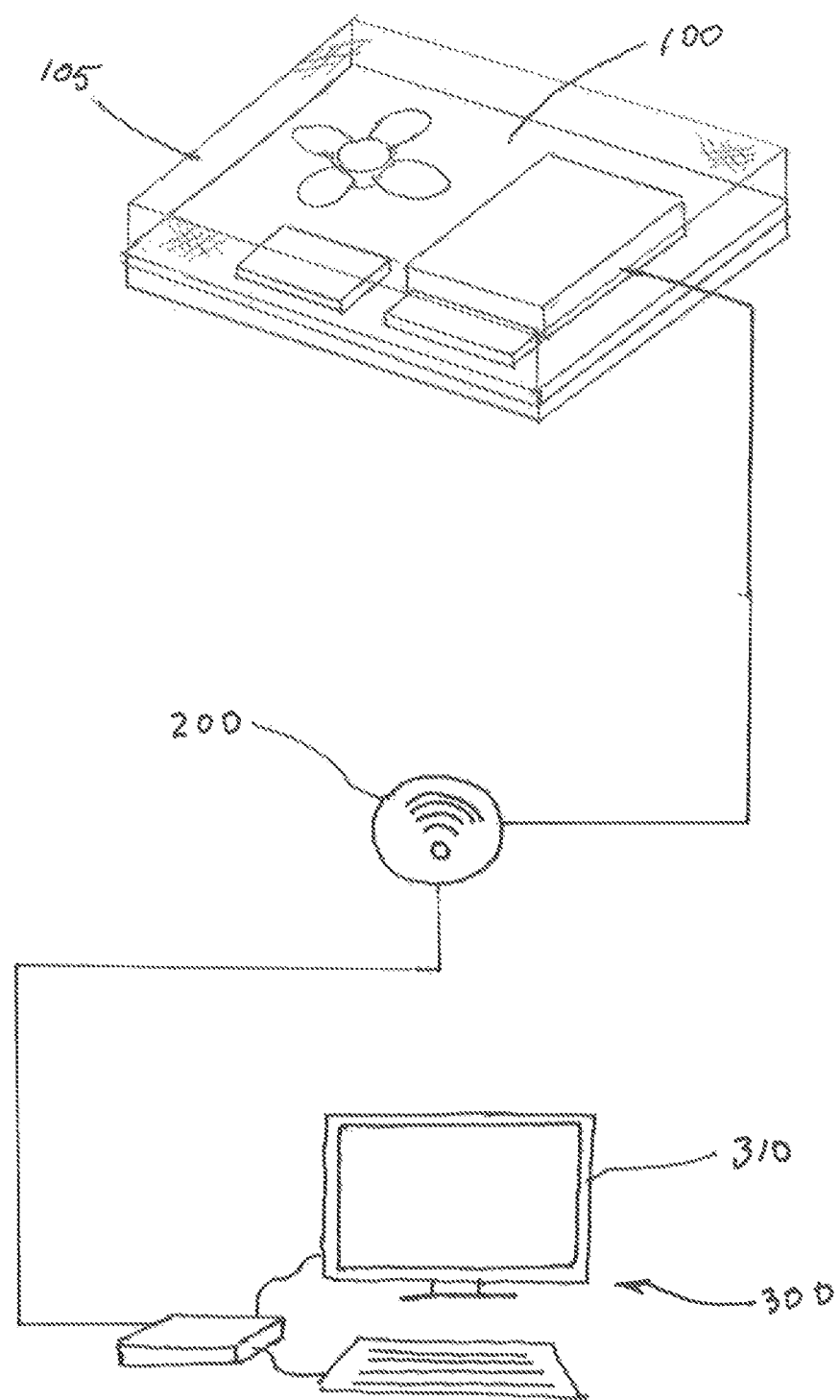
FIG. 1 depicts the vaping alert system of the present invention.

FIG. 1 schematically illustrates the system of the present invention, which includes a sensor assembly 100, a network 200, and a digital device 300 that has a display 310 on which alerts can be posted.

Figure 2:
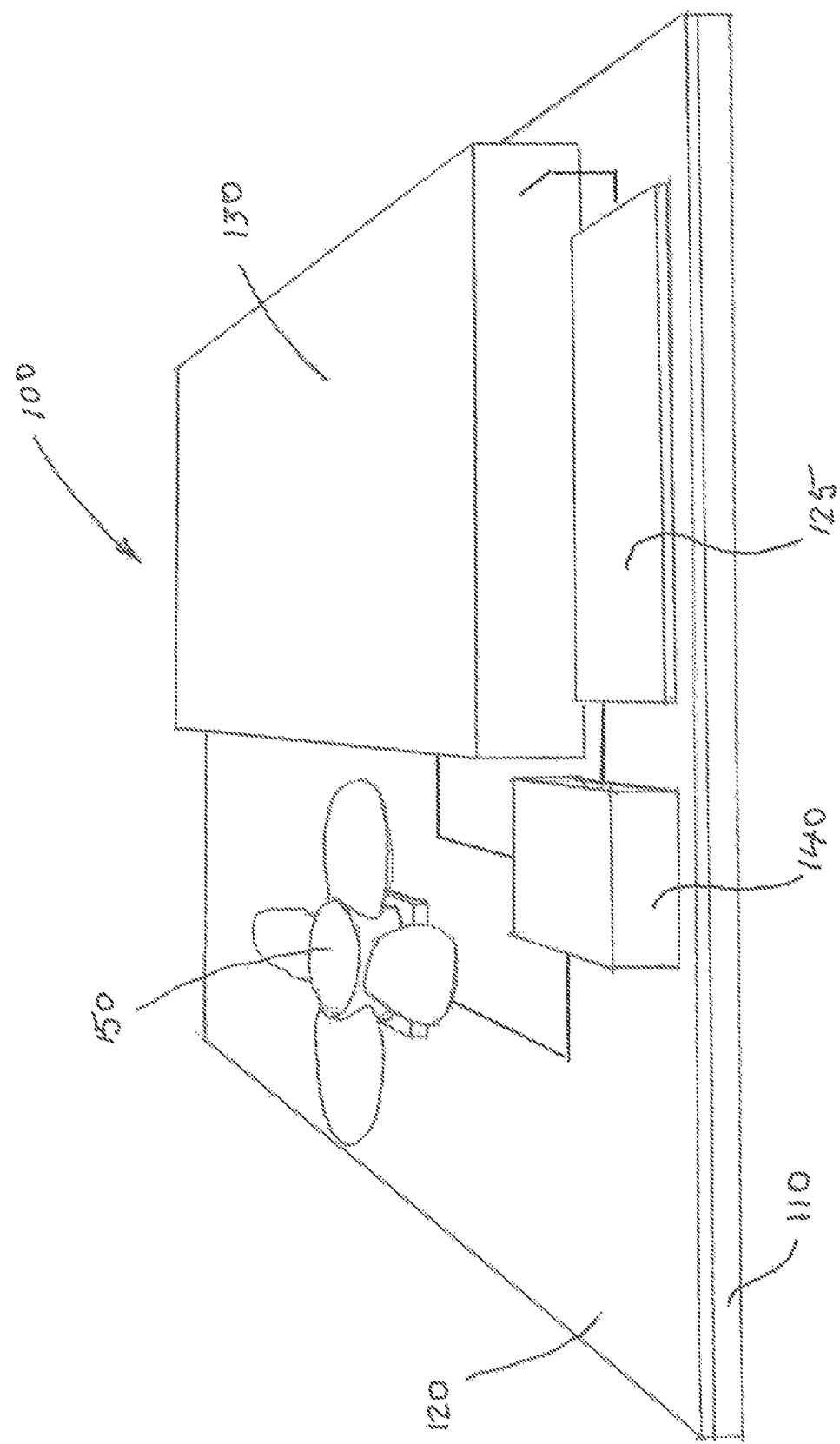
FIG. 2 depicts an embodiment of the sensor assembly of the present invention.

FIG. 2 schematically illustrates in greater detail the sensor assembly 100. As can be seen in that figure, sensor assembly 100 includes a baseboard 110, a sensor film 120, a transducer 125, a microcontroller 130, a power supply 140 and an air circulator 150. Preferably sensor assembly 100 is compact, for example 3 inches by 5 inches, and is adapted to be mounted on a wall, ceiling or floor of a confined area, such as a school bathroom. The sensor assembly 100 preferably is enclosed in a mesh 105 (shown in FIG. 1) to protect it, yet permit the ingress of air from the surroundings.

The baseboard 110 of sensor assembly 100 preferably has a planar rectangular shape and is formed from a relatively rigid material, such as PVC (polyvinyl chloride), so that baseboard 110 acts as the backbone of sensor assembly 100 and provides a platform for securing the other components of sensor assembly 100 firmly in place.

A sensor film 120, shown in FIG. 2, is positioned on and secured to the baseboard 110. The sensor film 120 is characterized by having a property that changes a measurable amount upon exposure to the nicotine typically contained in the atmosphere of a room or other confined space arising from the use of vaping products. The sensor film 120 can be for example a polyaniline film with an emeraldine surface doped with formic acid. The sensor film 120, when exposed to nicotine in the atmosphere, will absorb nicotine and thereby exhibit a change in a property, such as by exhibiting an increase in density.

The transducer 125 shown in FIG. 2 is associated with the sensor film 120 (as by being affixed to film 120) so as to monitor the property of interest for change. For example, in the case where the property of interest is density, the transducer 125 would be a density transducer. The transducer 125 produces an electrical signal indicative of a change in the property of interest.

Microcontroller 130 is also mounted on baseboard 110. Microcontroller 130 is electrically connected to the transducer 125 for receiving the electrical signal indicative of a change in the property of interest. The microcontroller 130 is additionally provided with appropriate input/output functionality for communicating with network 200. Given that sensor assembly 100 may be used in facilities where wired networks may not be located, such as in lavatories, it is preferred that microcontroller 130 be adapted to communicate with a wireless network (such as network 200 shown in FIG. 1), using for example User Data Protocol (UDP). Microcontroller 130 is provided with an internally stored program that causes transmission to network 200 of an appropriate UDP message when there is a change in the property of interest above a preselected threshold.

In the embodiment shown in FIG. 2, there is provided a power supply 140 for energizing the microcontroller 130 and transducer 125 as necessary. Power supply 140 shown in FIG. 2 is a battery, which is preferably positioned at a location allowing easy access to permit periodic replacement. Optionally, there can be provided a power line connection to an electrical outlet (together with any necessary voltage transformer and AC/DC converter), either with a battery as a backup to ensure that sensor assembly 100 is always functional, or in lieu of a battery. It is also possible to utilize a solar cell as power supply 140, either alone or in conjunction with a battery and/or a power line connection, if sensor assembly 100 is positioned at a sufficiently illuminated location, such as near a window or near overhead lighting.

As shown in FIG. 2, sensor assembly 100 additionally includes an air circulator 150, which in the embodiment shown is a fan positioned over sensor film 120 and proximate to microcontroller 130. The air circulator 150 is to assist moving air from the surrounding region over sensor film 120 beyond what would arise from gaseous diffusion and room air currents. The goal of utilizing air circulator 150 is to make the process of detecting the nicotine more efficient and faster, as it is intended to reduce or eliminate the need for sensor assembly 100 being in close proximity to the subject engaged in vaping. Preferably the air circulator 150 would always be on, to better ensure that any nicotine in the surrounding atmosphere would be detected. The fan in the embodiment shown in the figures is energized by power supply 140. It is preferred that neither the fan nor the other components of sensor assembly 100 make any noises (like a smoke detector). A vaping subject would therefore less likely be aware of the sensor assembly's presence, thereby reducing the potential for a malefactor disabling sensor assembly 100.

One or more sensor assemblies 100 can be positioned at locations in controlled facilities where unauthorized vaping may occur. Thus in the case of schools, a sensor assembly 100 can be positioned in each student bathroom of concern. When a sensor assembly 100 detects nicotine, an alert message is sent from the microcontroller 130 via network 200 to receiving digital device 300 (desktop, smart phone, etc.) having display 310, which is monitored by an authoritative figure from the school. In the situation where there are multiple sensor assemblies at different locations, each location can be assigned an identifier, which can be included in the stored program resident with the associated microcontroller 130. This location would then be transmitted with the alert message, and thereby enable school officials to see where the nicotine was coming from and eventually, who was using it.

The foregoing detailed description is for illustration only and is not to be deemed as limiting the inventions, which are defined in the appended claims.

What is claimed is:

1. A vaping alert system comprising:
    (a) a first sensor assembly including:
        (1) a baseboard,
        (2) a sensor film secured to the baseboard which has a property of interest that changes a measurable amount upon exposure to a level of nicotine in an atmosphere of a confined space, as arises from the use of an electronic cigarette therein,
        (3) a density transducer associated with the sensor film for detecting a change in the property of interest and generating an electrical signal indicative of a change in the property of interest, wherein the property of interest is a density of the sensor film,
        (4) a microcontroller programmed for receiving the electrical signal indicative of a change in the property of interest and for generating an alert when the property of interest exceeds a preselected threshold level,
        (5) an air circulator to assist moving air from the surrounding region over the sensor film, and
        (6) a power supply for energizing the microcontroller and the air circulator;
    (b) a digital device having a display for providing a notification to a custodian thereof when an alert is generated; and
    (c) a computer network, connected to the microcontroller of the first sensor assembly and connected to the digital device, for communicating the alert from the microcontroller of the first sensor assembly to the digital device.

2. The vaping alert system of claim 1, wherein the computer network is a wireless computer network.

3. The vaping alert system of claim 1, wherein the first sensor assembly is located in a first room of a structure having plural rooms, and further comprising (d) a second sensor assembly that includes components (1)-(6) as in the first sensor assembly, the second sensor assembly located in a second room of the structure, with the computer network additionally connected to the microcontroller of the second sensor assembly for communicating the alert from the microcontroller of the second sensor assembly to the digital device.

4. The vaping alert system of claim 3, wherein the microcontroller of the first and second sensor assemblies is each programmed to generate an alert, when the property of interest exceeds a preselect threshold level, which identifies the room in which the property of interest has exceeded the threshold level.

5. The vaping system of claim 1, wherein the power supply comprises a removable battery.

6. The vaping system of claim 5, wherein the power supply further comprises an electrical connection adapted to receive electricity supplied by an electric utility.

7. The vaping system of claim 1, wherein the sensor film comprises a polyaniline film.

8. A sensor assembly for a vaping alert system comprising:
    a baseboard,
    a sensor film secured to the baseboard which has a property of interest that changes a measurable amount upon exposure to a level of nicotine in an atmosphere of a confined space, as arises from the use of an electronic cigarette therein,
    a density transducer associated with the sensor film for detecting a change in the property of interest and generating an electrical signal indicative of a change in the property of interest, wherein the property of interest is a density of the sensor film,
    a microcontroller programmed for receiving the electrical signal indicative of a change in the property of interest and for generating an alert when the property of interest exceeds a preselected threshold level, the microcontroller adapted to be connected to a computer network for communicating the alert from the microcontroller to a digital device having a display for providing a notification to a custodian thereof when an alert is generated;

an air circulator to assist moving air from the surrounding region over sensor film, and a power supply for energizing the microcontroller and the air circulator.

9. The sensor assembly of claim 8, wherein the air circulator is a fan powered by the power supply.

10. The vaping system of claim 8, wherein the power supply comprises a removable battery.

11. The vaping system of claim 8, wherein the sensor film comprises a polyaniline film.

\* \* \* \* \*